(12) United States Patent
Ohno et al.

(10) Patent No.: US 8,148,379 B2
(45) Date of Patent: *Apr. 3, 2012

(54) THERAPEUTIC AGENT FOR SENILE DEMENTIA

(75) Inventors: Yukihiro Ohno, Osaka (JP); Takeo Ishiyama, Suita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/140,927

(22) Filed: Jun. 17, 2008

(65) Prior Publication Data

US 2008/0255148 A1 Oct. 16, 2008

Related U.S. Application Data

(62) Division of application No. 10/562,039, filed as application No. PCT/JP2004/009095 on Jun. 22, 2004, now abandoned.

(30) Foreign Application Priority Data

Jun. 23, 2003 (JP) ................................ 2003-178386

(51) Int. Cl.
*A61K 31/497* (2006.01)
(52) U.S. Cl. ................................. 514/254.04
(58) Field of Classification Search .................. None
See application file for complete search history.

(56) References Cited

U.S. PATENT DOCUMENTS

| | | | |
|---|---|---|---|
| 5,444,073 | A | 8/1995 | Perregaard et al. |
| 5,532,372 | A | 7/1996 | Saji et al. |
| 5,780,632 | A | 7/1998 | Saji et al. |
| 6,964,962 | B2 | 11/2005 | Wong et al. |
| 7,067,507 | B2 | 6/2006 | Pulley et al. |
| 2003/0050307 | A1 | 3/2003 | Ruhland et al. |
| 2009/0176800 | A1* | 7/2009 | Ishiyama ............. 514/254.04 |

FOREIGN PATENT DOCUMENTS

| | | |
|---|---|---|
| EP | 0 464 846 A1 | 1/1992 |
| EP | 464846 | 1/1992 |
| JP | 8-333368 A | 12/1996 |
| JP | 2003-135074 A | 5/2003 |
| JP | 2003-160583 | 6/2003 |
| JP | 2003-519226 A | 6/2003 |
| WO | WO 93/16073 A1 | 8/1993 |
| WO | WO 95/34306 | 12/1995 |
| WO | WO-96/14297 A1 | 5/1996 |
| WO | WO 99/52519 | 10/1999 |
| WO | WO 02/22581 A1 | 3/2002 |
| WO | WO-02/24166 | 3/2002 |
| WO | WO 02/24166 A1 | 3/2002 |
| WO | WO 03/066039 A1 | 8/2003 |

OTHER PUBLICATIONS

Kahle et al. Emerging Therapeutic Targets, 2001, 5(1), 125-132.*
Parnetti et al. Journal of the Neurological Sciences, 2007, 257, 264-69.*
Doggrell et al. Expert Opinion on Investigational Drugs, 2003, 12(10), 1633-54.*
"Delirium, Dementia, Amensia, Cognitive Disorders", http://www.nlm.nih.gov/cgi/mesh/2009/MB_cgi?mode=&term...m,+Dementia,+Amnestic,+Cognitive+Disorders&field=entry, accessed Jul. 1, 2009.*
Friedman. Psychopharmacology, 2004, 174, pp. 45-53.*
Emre et al. The New England Journal of Medicine, 2004, 351:24, pp. 2509-2518.*
Fernandez et al. Expert Opinion on Pharmacotherapy, 2003, 4(11), pp. 2027-2037.*
Small. Expert Opinion on Emerging Drugs, 2005, 10(4), 817-823.*
Rinsho-Seishinigaku (Clinical Psychiatry), 31 (10): 1189-1193 (2002).
Tokita et al., "Combination of a novel antidementia drug FK960 with donepezil synergistically improves memory deficits in rats," *Pharmacology, Biochemistry and Behavior*, vol. 73 (2002), pp. 511-519.
Thomas et al., "Specific impairments in visuospatial working and short-term memory following low-dose scopolamine challenge in healthy older adults," Neuropsychologia, vol. 46 (2008), pp. 2476-2484.
D. M. Bowen, Traditional pharmacotherapy may succeed in Alzheimer's disease, Trends in Neurosciences, 1992, vol. 15, No. 3, pp. 84-85.
Tokita, Kenichi et al., "Combination of a novel antidementia drug FK960 with donepezil synergistically improves memory deficits in rats", Pharmacology, Biochemistry and Behavior, 2002, vol. 73, pp. 511-519.

(Continued)

*Primary Examiner* — Noble Jarrell
(74) *Attorney, Agent, or Firm* — Finnegan, Henderson, Farabow, Garrett & Dunner, LLP

(57) ABSTRACT

A therapeutic/preventive agent for cognitive dysfunctions, which comprises as an active ingredient an imide derivative of the following formula [1]:

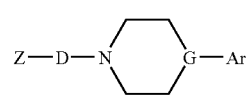

[1]

wherein Z is a group of the formula [2]:

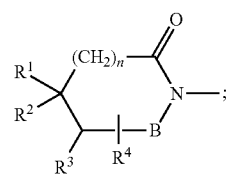

[2]

D is a group of —$(CH_2)_p$-A-$(CH_2)_q$—; G is =N—, —CH—, etc.; and Ar is an aromatic heterocyclic group, etc.

4 Claims, 2 Drawing Sheets

OTHER PUBLICATIONS

Kahle, Philipp J. et al., "The emerging utility of animal models of chronic neurodegenerative diseases", Emerging Therapeutic Targets, 2001, vol. 5, No. 1, pp. 125-132.
Duka, Theodora "Scopolamine-induced amnesia in humans: lack of effects of the benzodiazepine receptor antagonist β-carboline ZK 93426", Journal of Psychopharmacology, 1992, vol. 6, No. 3, pp. 382-388, Abstract.
Norman et al. Journal of Medical Chemistry, 1996, 39(1), 149-57.
Taixiang, Xu, et al., "Status quo and Development of Alzheimer's Disease," ACTA Academiae Medecinae Qingdao Universitatis, vol. 37, No. 4, pp. 355-357 (2001).
Ishizumi, K. et al., *Chem. Pharm. Bull.* 43(12):2139-2151 (1995).
Fabre, S. et al., *Bioorg. Med. Chem.* 1(3):193-196 (1993).
Miyachi, H. et al., *J. Med. Chem.* 40:2858-2865 (1997).
Botero Cid, H. et al., *J. Med. Chem.* 43:2155-2164 (2000).
Ebihara, Mitsuru et al., Togo Shicchosho no Dobutsu Model, *Igaku no Ayumi*, vol. 208, No. 3, pp. 138-142 (2004).
Enomoto, Takeshi et al., Brain Science, vol. 25, No. 5, pp. 437-444 (2003).
Shinkei Kairomo Keisei to Kofunsei Synapse Kasosei ni Kansuru Kodagakuteki Kenkyu, pp. 13-20 (2003).
Jellinger, Kurt A., "The Pathology of Ischemic-Vascular Dementia: An Update," Journal of the Neurological Sciences 203-204 (2002) pp. 153-157.
The Lancet, Lancet Limited, London, GB LNKD-DOI:10.1016/S0140-6736 (01) 05083-8, vol. 208, No. 5381, Oct. 16, 1926, pp. 820-821.
EP Official Action for Corresponding EP Application No. 04 746 564.6-2117 dated Nov. 20, 2009.
EP Official Action for Corresponding EP Application No. 04 746 564.6-2117 dated Aug. 27, 2010.
Approval Labeling Text, NDA 21-487, for NAMENDA™ (memantine hydrochloride).
Barber, Teresa A., et al., Memantine ameliorates scopolamine-induced amnesia in chicks trained on taste-avoidance learning, *Neurobiology of Learning and Memory*, vol. 93, pp. 540-545 (2010).
Beier, Corina, et al., "Effect of rivastigmine on scopolamine-induced memory impairment in rats," *European Journal of Pharmacology*, vol. 383, pp. 231-240 (1999).
Clinton et al., *Am. J. Psychiatry*, vol. 160, No. 6, pp. 1100-1109, (Jun. 2003).
Clinton et al., *Society for Neuroscience*, Program No. 754.4, (2003). (online) (abstract only).
Cloninger, *Proc. Natl. Acad. Sci.*, vol. 99, No. 21, pp. 13365-13367, (Oct. 15, 2002).
Corbett, *Pharmacol. Biochem. Behav.*, vol. 51(2-3), p. 561-564, (1995).
Diagnostic and Statistical Manual of Mental Disorders, Fourth Edition (DSM-IV™) pp. 273-278, 285, and 286 (1994), published by the American Psychiatric Association, Washington D.C.
Didriksen, et al, Society Neuroscience Abstract, abstract No. 893.1 (2002).
English translation of Office Action from the Chinese Patent Office in Appln. No. 20040017534.X dated Jan. 29, 2010.
English translation of Office Action from the Japanese Patent Office in Appln. No. 2005-507314 dated Jun. 29, 2010.
Geyer et al., *Progress in Neuro-Psychopharmacology & Biological Psychiatry*, vol. 27, pp. 1071-1079, (2003).
Goff et al., *Am. J. Psychiatry*, vol. 158, No. 9, pp. 1367-1377, (Sep. 2001).
Harrod et al., *Pharmacology, Biochemistry, and Behavior*, vol. 69, pp. 585-593, (2001).
Harvey et al., *Psychopharmacology*, vol. 169, pp. 213-214, (2003).
Harvey et al., *J. Clin. Psychiatry*, vol. 65, pp. 361-372, (2004).
Hyman et al., *Science*, vol. 299, pp. 350-351, (Jan. 17, 2003).
Ibrahim et al., *Am. J. Psychiatry*, vol. 159, No. 11, pp. 1811-1823, (Nov. 2000).
Kasper et al., *Psychoneuroendocrinology*, vol. 28, pp. 27-38, (2003).
Kay, Stanley R. et al., The Positive and Negative Syndrome Scale (PANSS) for Schizophrenia, *Schizophrenia Bulletin*, vol. 13, No. 2, 1987, pp. 261-276.
Krystal et al., *Psychopharmacology*, vol. 169, pp. 215-233, (2003).
Lindenmayer et al., *Psychiatric Quarterly*, vol. 65, No. 4, pp. 299-322 (1994).
Malenka et al., *Science*, vol. 285, pp. 1870-1874, (Sep. 17, 1999).
Meltzer et al., *Proc. Natl. Acad. Sci.*, vol. 96, No. 24, pp. 13591-13593, (Nov. 23, 1999).
Mettey Y, et al., "Synthesis of 11-Aminodibenzol[b,f][1,4]thiazepines and Fluoro Derivatives," *Journal of Heterocyclic Chemistry*, 03-04(34), pp. 465-467 (1997).
Misane et al., "Selective 5-$HT_{1A}$ Antagonists WAY 10065 and NAD-299 Attenuate the Impairment of Passive Avoidance Caused by Scopolamine in the Rat," *Neuropsychopharmacology* 28, pp. 253-264 (2003).
Miyamoto et al., *Journal of Neuroscience*, vol. 21, No. 2, pp. 750-757, (Jan. 15, 2001).
Moghaddam, *Neuron*, vol. 40, pp. 881-884, (Dec. 4, 2003).
Mohn et al., *Cell*, vol. 98, pp. 427-436, (1999).
Myhrer, *Brain Research Reviews*, vol. 41, pp. 268-287, (2003).
Nakagawa et al., *Brain Research*, vol. 706, pp. 227-232, (1996).
Noda et al, *Abstracts Society Neuroscience*, vol. 26(1-2), p. 6533 (2000).
Office Action in U.S. Appl. No. 10/525,021 mailed Dec. 17, 2007.
Office Action in U.S. Appl. No. 10/525,021 mailed Sep. 17, 2008.
Office Action in U.S. Appl. No. 10/525,021 mailed Jun. 12, 2009.
Office Action in U.S. Appl. No. 10/525,021 mailed Mar. 5, 2010.
Office Action in U.S. Appl. No. 10/562,039 mailed Mar. 18, 2008.
Office Action in U.S. Appl. No. 10/589,804 mailed Dec. 11, 2008.
Office Action in U.S. Appl. No. 12/401,958 (continuation of U.S. Appl. No. 10/589,804) mailed Oct. 1, 2009.
Office Action in U.S. Appl. No. 12/401,958 mailed Apr. 5, 2010.
*Perricone v. Medicis Pharm. Corp.*, 432 F.3d 1368 (Fed. Cir. 2005).
Prescribing Information for ARICEPT® (donepezil hydrochloride) (14 pages) (2010).
Prescribing information for "Exelon® (rivastigmine tartrate) Capsules and Oral Solution" (31 pages) (2006).
Puttrese, et al. *Society Neuroscience Abstract*, v. 2003, abstract No. 964.19 (2003).
Sharma et al., *Psychiatr. Clin. N. Am.*, vol. 26, pp. 25-40, (2003).
Tokuda, et al, *J. Pharmacal Sciences*, vol. 94, supplement 1, p. 163P (2004).
Turetsky et al., "Memory-Delineated Subtypes of Schizophrenia: Relationship to Clinical, Neuroanatomical, and Neurophysiological Measures," *Neuropsychology* vol. 16, No. 4, pp. 481-490 (2002).
U.S. Appl. No. 10/525,021, filed Feb. 18, 2005.
U.S. Appl. No. 10/562,039, filed Dec. 22, 2005.
U.S. Appl. No. 10/589,804, filed Aug. 17, 2006.
Weiss et al., *Psychopharmacology*, vol. 162, pp. 11-17, (2002).
Wise et al, *Society Neuroscience Abstract*, vol. 2002, abstract No. 494.7 (2002).
Xu Taixiang et al, "Status quo and Development of Alzheimer's Disease," *Acta Academiae Medicinae Qingdao Universitatis*, vol. 37, No. 4, p355-357 (2001).
Romero, Arthur G. et al., "Synthesis of Metabolically Stable Arylpiperazine 5-$HT_{1A}$ Receptor Agonists," Bioorganic & Medicinal Chemistry Letters, vol. 2, No. 12, pp. 1703-1706 (1992).
European Search Resort for European Patent Application No. 04746564.6, Aug. 27, 2010.

* cited by examiner

THERAPEUTIC AGENT FOR SENILE DEMENTIA

This application is a Divisional of application Ser. No. 10/562,039 filed on Dec. 22, 2005, which is a national phase application of International Application No. PCT/JP2004/009095 filed on Jun. 22, 2004, which claims priority to JP 2003/178386 filed in Japan on Jun. 23, 2003 under 35 U.S.C. §119; the entire contents of all are hereby incorporated by reference.

TECHNICAL FIELD

The present invention relates to a therapeutic agent for dementia, more particularly, a therapeutic agent for dementia, which comprises as an active ingredient an imide derivative.

BACKGROUND ART

Senile dementia is divided broadly into the Alzheimer type dementia and the cerebrovascular dementia, and about 80% of the patients of senile dementia can be classified into these categories. As the population rapidly ages, the number of the patients of senile dementia demonstrates an upward trend in these days. In Japan, it is speculated that about 7% of the people 65 years old or over show the symptoms of dementia, and hence, it is an urgent need to develop an excellent therapeutic agent for dementia. The Alzheimer type dementia is accompanied by senile plaque and neurofibrillary tangle, and it is pathologically characterized by encephalatrophy caused by significant neuronal death. In familial Alzheimer's disease, several gene mutations have been identified, whereby a leading hypothesis for neuronal pathogenetic mechanism thereof has been speculated, but the most of cases are sporadic, and hence, it may be said that Alzheimer's disease is still a disease of unknown cause. Accordingly, at the present, there is no radical therapeutic method for inhibiting neurodegeneration. The Alzheimer type dementia shows as core symptoms cognition dysfunctions L such as disorders of memory, faculty of orientation, attention, etc., and it is also accompanied by peripheral symptoms such as psychotic manifestations or abnormal behavior problems (e.g., depression, aggressive attack, delusion, etc.). In the symptomatic treatment of these symptoms, only an acetylcholine esterase inhibitor has been clinically used, and it has been reported that acetylcholine esterase inhibitors are also effective to not only core symptoms but also peripheral symptoms. In the treatment with acetylcholine esterase inhibitors, neurotransmitter acetylcholine is supplemented by inhibiting acetylcholine-degrading enzyme, while acetylcholine neuronal cells, which are closely-linked with cognitive function, are especially disturbed in Alzheimer's disease and neurotransmitter acetylcholine is reduced.

On the other hand, the cerebrovascular dementia is a disease which develops owing to cerebrovascular disorders, and at the moment, there is no cure for core symptoms thereof. However, recently, the clinical trial of acetylcholine esterase inhibitors has been done, and it has become apparent that these medicaments are also effective to cerebrovascular dementia. Accordingly, there is a possibility that a therapeutic agent having a similar therapeutic mechanism to the Alzheimer's disease such as acetylcholine esterase inhibitors may be effective even to cerebrovascular dementia (e.g., Rinsho-Seishinigaku (i.e., Clinical Psychiatry), 31 (10): 1189-1193 (2002)).

On the other hand, there has not been known any therapeutic agent which shows no acetylcholine esterase inhibitory activity but is effective to senile dementia such as the Alzheimer type dementia and the cerebrovascular dementia. Moreover, JP Patent No. 2800953 discloses imide derivatives showing an excellent antipsychotic activity and anxiety reducing activity, but it has never indicated whether or not those derivatives show effects on senile dementia.

DISCLOSURE OF INVENTION

The present invention provides a therapeutic agent for senile dementia. More particularly, the present invention provides a therapeutic agent effective to both of the core symptoms and the peripheral symptoms of senile dementia.

The present inventors have intensively studied in order to solve the above problems, and found that the imide compound of the present invention exhibits a therapeutic effect in cognitive/memory disturbance models produced by acetylcholine receptor blocker, which are representative animal models for senile dementia, and finally they have accomplished the present invention.

Namely, the present invention relates to the following:
(1) A therapeutic/preventive agent for cognitive dysfunctions, which comprises as an active ingredient an imide derivative of the formula [1]:

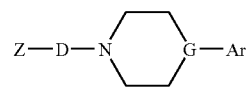

{wherein Z is a group of the formula [2]:

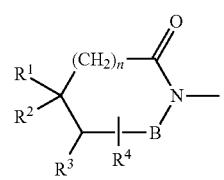

(in which B is a carbonyl or a sulfonyl; $R^1$ $R^2$, $R^3$ and $R^4$ are independently a hydrogen atom or a lower alkyl, provided that $R^1$ and $R^2$, or $R^1$ and $R^3$ may combine each other to form a hydrocarbon ring, or $R^1$ and $R^3$ may combine each other to form an aromatic hydrocarbon ring; said hydrocarbon ring may optionally be cross-linked with a lower alkylene or an oxygen atom; said lower alkylene and hydrocarbon ring may optionally be substituted by at least one alkyl; and n is 0 or 1), D is a group of the formula [3]:

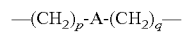

(in which A is a hydrocarbon ring optionally be cross-linked with a lower alkylene or an oxygen atom; said lower alkylene and hydrocarbon ring may optionally be substituted by at least one alkyl; and p and q are independently 0, 1 or 2), G is N, CH or COH, and —Ar is an aromatic heterocyclic group, an aromatic hydrocarbon group, benzoyl, phenoxy, or phenylthio, or G is a carbon atom, and —Ar is biphenylmethylidene, where said aromatic heterocyclic group, aromatic hydrocarbon group, benzoyl, phenoxy or phenylthio, and biphenylmethylidene may optionally be substituted by at least one group selected from a lower alkyl, a lower alkoxy and a halogen atom},
or an acid addition salt thereof.
(2) The therapeutic/preventive agent for cognitive dysfunctions according to the above (1), which is a therapeutic agent for senile dementia.

(3) A therapeutic/preventive agent for cognitive dysfunctions, which comprises as an active ingredient an imide derivative of the above formula [1], wherein —Ar is an aromatic heterobicyclic group, naphthyl, benzoyl, phenoxy or phenylthio and G is N, CH or COH, or —Ar is biphenyl-methylidene and G is a carbon atom (said aromatic heterobicyclic group, naphthyl, benzoyl, phenoxy, phenylthio and biphenylmethylidene may optionally be substituted by at least one group selected from a lower alkyl, a lower alkoxy and a halogen atom), or an acid addition salt thereof.

(4) The therapeutic/preventive agent for cognitive dysfunctions according to the above (3), which is a therapeutic agent for senile dementia.

(5) A therapeutic/preventive agent for cognitive dysfunctions, which comprises as an active ingredient an imide derivative of the above formula [1], wherein —Ar is an aromatic heterocyclic group condensed with a benzene ring, or naphthyl, benzoyl, phenoxy or phenylthio (said aromatic heterocyclic group condensed with a benzene ring, naphthyl, benzoyl, phenoxy, and phenylthio may optionally be substituted by at least one group selected from a lower alkyl, a lower alkoxy and a halogen atom), and G is N, CH or COH, or an acid addition salt thereof.

(6) The therapeutic/preventive agent for cognitive dysfunctions according to the above (5), which is a therapeutic agent for senile dementia.

(7) A therapeutic/preventive agent for cognitive dysfunctions, which comprises as an active ingredient an imide derivative of the above formula [1], wherein Z is a group of the formula [4]:

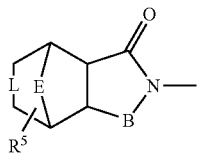

[4]

in which -L- is a single bond or a double bond, E is a lower alkylene optionally substituted by a lower alkyl, or an oxygen atom, $R^5$ is a hydrogen atom or a lower alkyl, and B is the same as defined in the above (1);
a group of the formula [5]:

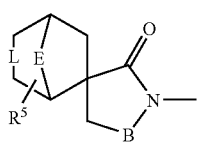

[5]

in which -L-, E, $R^5$ and B are as defined above;
a group of the formula [6]:

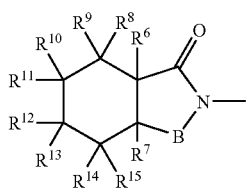

[6]

in which $R^6$, $R^7$, $R^8$, $R^9$, $R^{10}$, $R^{11}$, $R^{12}$, $R^{13}$, $R^{14}$, $R^{15}$ are independently a hydrogen atom or a lower alkyl, or the adjacent two groups of $R^6$, $R^7$, $R^8$, $R^9$, $R^{10}$, $R^{11}$, $R^{12}$, $R^{13}$, $R^{14}$, $R^{15}$ may combine each other to form a double bond, and B is as defined above;
a group of the formula [7]:

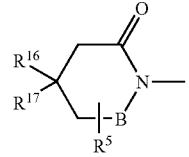

[7]

in which $R^{16}$ and $R^{17}$ are independently a hydrogen atom or a lower alkyl, or $R^{16}$ and $R^{17}$ may combine each other to form a saturated hydrocarbon ring, and $R^5$ and B are as defined above; or
a group of the formula [8]:

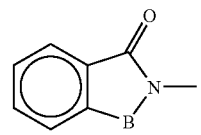

[8]

in which B is as defined above,
or an acid addition salt thereof.

(8) The therapeutic/preventive agent for cognitive dysfunctions according to the above (7), which is a therapeutic agent for senile dementia.

(9) A therapeutic/preventive agent for cognitive dysfunctions, which comprises as an active ingredient an imide derivative of the formula [9]:

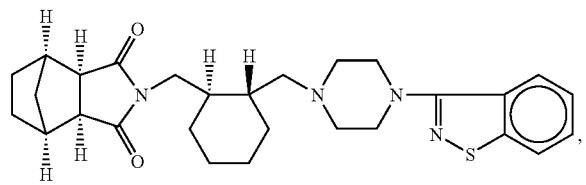

[9]

or an acid addition salt thereof.

(10) The therapeutic/preventive agent for cognitive dysfunctions according to the above (9), which is a therapeutic agent for senile dementia.

(11) The therapeutic/preventive agent for cognitive dysfunctions according to the above (2), (4), (6), (8) or (10), which is a therapeutic agent for the Alzheimer type dementia.

(12) The therapeutic/preventive agent for cognitive dysfunctions according to the above (2), (4), (6), (8) or (10), which is a therapeutic agent for the cerebrovascular dementia.

BEST MORE FOR CARRYING OUT THE INVENTION

Figure 1:
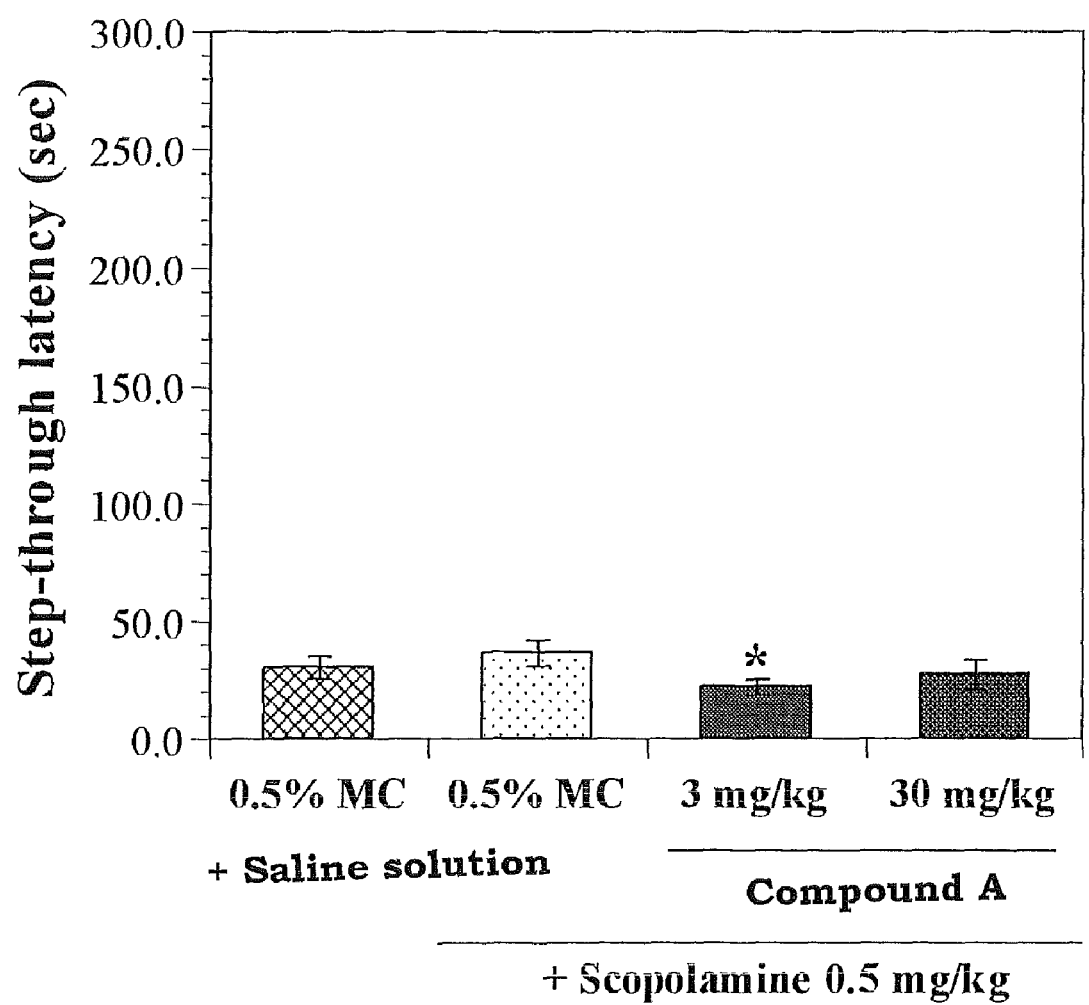
FIG. 1 shows the effects of the imide derivative on rats in one step-through passive avoidance test where the acetylcholine receptor blocker scopolamine was used for inducing amnesia, and indicates the step-through latency during the training (*: P<0.05 vs the group treated with 0.5% MC+scopolamine (Steel's test)).

Each group of the imide derivative of the formula [1] of the present invention are explained in detail.

The lower alkylene for Z and A includes, for example, ones having not more than 3 carbon atoms such as methylene, ethylene, trimethylene, etc.

The hydrocarbon ring for Z and A includes, for example, a cycloalkane or cycloalkene having not more than 7 carbon atoms. The cycloalkane having not more than 7 carbon atoms includes, for example, cyclopropane, cyclobutane, cyclopentane, cyclohexane, cycloheptane, etc. The cycloalkene having not more than 7 carbon atoms includes, for example, cyclopentene, cyclohexene, cycloheptene, etc.

The hydrocarbon ring being cross-linked with a lower alkylene or an oxygen atom for Z and A includes, for example, rings having not more than 10 carbon atoms such as bicyclo[1.1.1]pentane, bicyclo[2.1.1]hexane, bicyclo[2.1.1]hex-2-ene, bicyclo[2.2.1]heptane, bicyclo[2.2.1]hept-2-ene, bicyclo[2.2.2]octane, bicyclo[2.2.2]oct-2-ene, bicyclo[4.1.1]octane, bicyclo-[4.1.1]oct-2-ene, bicyclo[4.1.1]oct-3-ene, bicyclo[3.2.1]octane, bicyclo-[3.2.1]oct-2-ene, bicyclo[3.2.1]oct-3-ene, bicyclo[3.2.1]oct-6-ene, bicyclo-[3.2.2]nonane, bicyclo[3.2.2]non-2-ene, bicyclo[3.2.2]non-3-ene, bicyclo-[3.2.2]non-6-ene, 2-oxabicyclo[1.1.1]butane, 2-oxabicyclo[2.1.1]pentane, 2-oxabicyclo[2.1.1]pent-4-ene, 7-oxabicyclo[2.2.1]hexane, 7-oxabicyclo-[2.2.1]-hex-2-ene, 7-oxabicyclo[4.1.1]heptane, 7-oxabicyclo[4.1.1]hept-2-ene, 7-oxabicyclo[4.1.1]hept-3-ene, 8-oxabicyclo[3.2.1]heptane, 8-oxabicyclo[3.2.1]hept-2-ene, 8-oxabicyclo[3.2.1]hept-3-ene, 8-oxabicyclo-[3.2.1]hept-6-ene, etc.

The aromatic hydrocarbon ring for Z includes, for example, ones having not more than 10 carbon atoms such as phenyl ring, naphthyl ring, etc.

The binding position of the hydrocarbon ring for A includes, for example, -1, 1-, -1,2-, -1,3-, -1,4-, etc.

The aromatic hydrocarbon group for —Ar includes, for example, L ones having not more than 10 carbon atoms such as phenyl, naphthyl, etc. The aromatic heterocyclic group for —Ar includes, for example, an aromatic heteromonocyclic group and an aromatic heterobicyclic group.

The aromatic heteromonocyclic group includes, for example, ones halving not more than 6 carbon atoms, and further having the same or different 1 to 4 heteroatoms selected from a nitrogen atom, an oxygen atom and a sulfur atom, such as pyridyl, pyrimidinyl, thiazolyl, oxazolyl, isoxazolyl, isothiazolyl, furyl, imidazolyl, etc.

The aromatic heterobicyclic group includes, for example, ones having not more than 10 carbon atoms, and further having the same or different 1 to 5 heteroatoms selected from a nitrogen atom, an oxygen atom and a sulfur atom, such as benzolog-fused rings (e.g., benziso-thiazolyl, benzisoxazolyl, benzofuryl, quinolyl, isoquinolyl, indolyl, imdazolyl, benzimidazolyl, benzoxazolyl, etc.), naphthyridinyl, puteridinyl, thienofuranyl, imidazothiophen-yl, imidazofuranyl, etc.

The alkyl includes, for example, ones having not more than 6 carbon atoms, and preferably lower alkyl groups having not more than 4 carbon atoms, such as methyl, ethyl, propyl, 2-propyl, butyl, etc. The lower alkyl includes, for example, ones having not more than 4 carbon atoms, such as methyl, ethyl, propyl, 2-propyl, butyl, etc.

The lower alkoxy includes, for example, ones having not more than 4 carbon atoms, such as methoxy, ethoxy, propoxy, 2-propoxy, butoxy, etc.

The halogen atom is fluorine, chlorine, bromine, iodine.

The present compound [1] may have stereoisomers and/or an optical isomer. The present invention also includes a mixture of these isomers or each isolated isomer.

The preferable group for —Ar is an aromatic heterobicyclic group, or naphthlyl, benzoyl, phenoxy or phenylthio (in these cases, G is N, CH, or COH), or biphenylmethylidene (in this case, G is a carbon atom), where said aromatic heterobicyclic group, naphthyl, benzoyl, phenoxy, phenylthio and biphenylmethylidene may optionally be substituted by at least one group selected from a lower alkyl, a lower alkoxy and a halogen atom.

The more preferable group for —Ar is a benzolog-fused ring, naphthlyl, benzoyl, phenoxy, or phenyl (said benzolog-fused ring, naphthyl, benzoyl, phenoxy, and phenylthio may optionally be substituted by at least one group selected from a lower alkyl, a lower alkoxy and a halogen atom), and in this case, G is N, CH or COH.

The further preferable group for —Ar is benzisothiazolyl, benzisoxazolyl, isoquinolyl, benzofuranyl, indazolyl or indolyl (said benzisothiazolyl, benzisoxazolyl, isoquinolyl, benzofuranyl, indazolyl and indolyl may optionally be substituted by at least one group selected from a lower alkyl, a lower alkoxy and a halogen atom), and in this case, G is N, CH or COH.

The preferable group for Z is, for example, a group of the formula [4]:

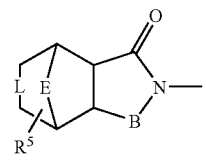

[4]

(in which -L- is a single bond or a double bond, E is a lower alkylene optionally substituted by a lower alkyl, or an oxygen atom, $R^5$ is a hydrogen atom or a lower alkyl, and B is a carbonyl or a sulfonyl);

a group of the formula [5]:

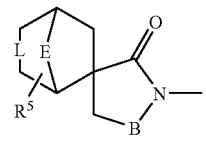

[5]

(in which -L-, E, $R^5$) and B are as defined above);

a group of the formula [6]:

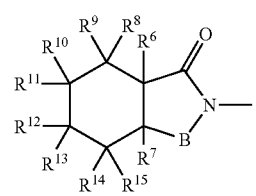

[6]

(in which $R^6$, $R^7$, $R^8$, $R^9$, $R^{10}$, $R^{11}$, $R^{12}$, $R^{13}$, $R^{14}$, $R^{15}$ are independently a hydrogen atom or a lower alkyl, or the adjacent two groups of $R^6, R^7, R^8, R^9, R^{10}, R^{11}, R^{12}, R^{13}, R^{14}, R^{15}$ may combine each other to form a double bond, and B is as defined above);

a group of the formula [7]:

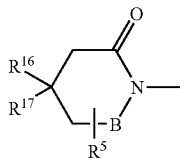

[7]

(in which $R^{16}, R^{17}$ are independently a hydrogen atom or a lower alkyl, or $R^{16}$ and $R^{17}$ may combine each other to form a saturated hydrocarbon ring, and $R^5$, and B are as defined above); or a group of the formula [8]:

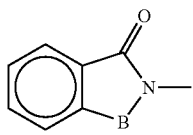

[8]

(in which B is as defined above), etc.

Then, the saturated hydrocarbon ring formed by combining $R^{16}$ and $R^{17}$ includes, for example, a cycloalkane having not more than 7 carbon atoms, such as cyclopropane, cyclobutane, cyclopentane, cyclohexane, cycloheptane, etc.

The preferable group for Z is, for example, a group of the formula [10]:

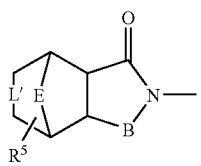

[10]

(in which -L'- is a single bond, E is a lower alkylene optionally substituted by a lower alkyl, or an oxygen atom, $R^5$ is a hydrogen atom or a lower alkyl, and B is a carbonyl or a sulfonyl);

a group of the formula [11]:

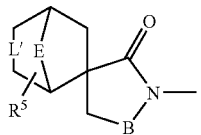

[11]

(in which -L'-, E, $R^5$ and B are as defined above);

a group of the formula [12]:

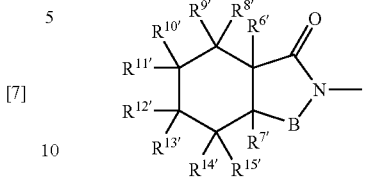

[12]

(in which $R^{6\prime}, R^{7\prime}, R^{8\prime}, R^{9\prime}, R^{10\prime}, R^{11\prime}, R^{12\prime}, R^{13\prime}, R^{14\prime}, R^{15\prime}$ are independently a hydrogen atom or a lower alkyl, and B is as defined above);

a group of the formula [7]:

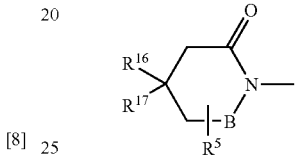

[7]

(in which $R^{16}, R^{17}, R^5$ and B are as defined above); or a group of the formula [8]:

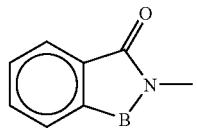

[8]

(B is as defined above).

The imide derivative of the present invention or an acid addition salt thereof may be prepared, for example, by the method disclosed in JP Patent No. 2800953 1 as mentioned above.

The imide derivative of the present invention may be used in the form of a pharmaceutically acceptable acid addition salt thereof. Inorganic acids such as hydrochloric acid, hydrobromic acid, sulfuric acid, etc. or organic acids such as fumaric acid, citric acid, tartaric acid, succinic acid, etc. may be exemplified as an acid for forming addition salts.

The imide derivative or a pharmaceutically acceptable acid addition salt thereof, which is the active compound of the present invention, may be administered at a dose suitable for necessity of each case in a conventional dosage form. For example, it can be administered orally in the form of tablets, capsules, syrups, suspension, etc. or parenterally in the form of injection preparation such as liquid preparations (e.g., solutions, emulsions, suspension, patches, etc.).

In addition, the above-mentioned suitable dosage forms may be prepared by mixing an active compound with a conventional pharmaceutically acceptable carriers, excipients, binders, stabilizers, etc. When used in the form of injection, it may additionally contain buffering agents, solubilizers, isotonic agents, etc.

The dose and the frequency of the administration of the present therapeutic agent may vary according to the dosage forms, or the severity of the diseases to be treated. For example, the imide derivative is orally administered at a dose of 1 to 200 mg per day in an adult, which is administered once a day or divided into several dosage units.

The diseases to which the therapeutic agent of the present invention is effective are the Alzheimer type and the cerebrovascular dementia, more particularly, various senile dementias (e.g., dementia with Lewy bodies, dementia from Pick's disease, dementia from Creutzfeldt-Jakob disease, dementia from Huntington's chorea, dementia from Parkinsorn's disease, etc.) including multiple infarct dementia, dementia ca used by cerebral infarction, Binswanger disease, dementia caused by stroke, amyloid angiopathy, ischemic dementia. Further, the therapeutic agent of the present invention shows the improving activity of cognitive dysfunctions accompanied by acetylcholine neuronal dysfunctions, and hence, it may be used in the treatment of traumatic cognitive dysfunctions, dementia in Down syndrome, schizophrenial cognitive dysfunctions, or cognitive dysfunctions accompanied by acetylcholine neuronal dysfunctions from any cause, in addition to the treatment of senile dementia.

EXAMPLES

The present invention is illustrated in more detail by Examples, but the present invention should not be construed to be limited thereto.

Example 1

Method

Male Wistar rats (7 weeks old) were used. As a test medicament, (1R,2S,3R,4S)—N-[(1R,2R)-2-[4-(1,2-benzisothiazol-3-yl)-1-piperazinyl-methyl]-1-cyclohexylmethyl]-2,3-bicycl[2.2.1]heptanedicarboxyimide (Compound A) was suspended in 0.5% methyl cellulose (MC) solution. As an agent for inducing amnesia, scopolamine (manufactured by Wako Pure Chemical Industries, Ltd., product No. 198-07901), which is an acethylcoline receptor blocker, was dissolved in saline solution (manufactured by TERUMO CORPORATION). Compound A at a dose of 3 mg/kg or 30 mg/kg, or 0.5% MC as a control was orally administered to the animals one hour prior to the training step in the one step-through passive avoidance test, and then, scopolamine at a dose of 0.5 mg/kg or a h saline solution as a control was subcutaneously administered to the animals 30 minutes prior to the training step. The volume of each solution to be administered was 5 ml/kg each.

The one step-through passive avoidance test in rats was carried out in the following manners with using an apparatus consisting of a light-dark box and an electric stimulator (manufactured by O'hara & Co., Ltd., product no. PA-2030A) as an experimental apparatus. Namely, on Day 1, after the medicament and the agent for inducing amnesia were administered, the rats were put into the light box of the experimental apparatus where the back of each rat was directed to the dark box. Then, 10 seconds later, a guillotine door set at the border between the dark box and the light box was opened. Due to the habits of the rats, once the rats entered into the dark box, the guillotine door was quickly closed. At three seconds after the entering into the dark box, an electroconvulsive shock (0.5 mA for 3 seconds) was given to the rats. Again, the guillotine door was opened, and after the rats spontaneously returned to the light box, the animals were transferred into the home cage. The period between the time just after the guillotine door was opened and the time at which the rats entered into the dark box was measured as a step-through latency. As to the animals which did not enter into the dark room even after 300 seconds, the training was terminated, and those animals were dropped in the following experiment for the reasons of training failure.

Figure 2:
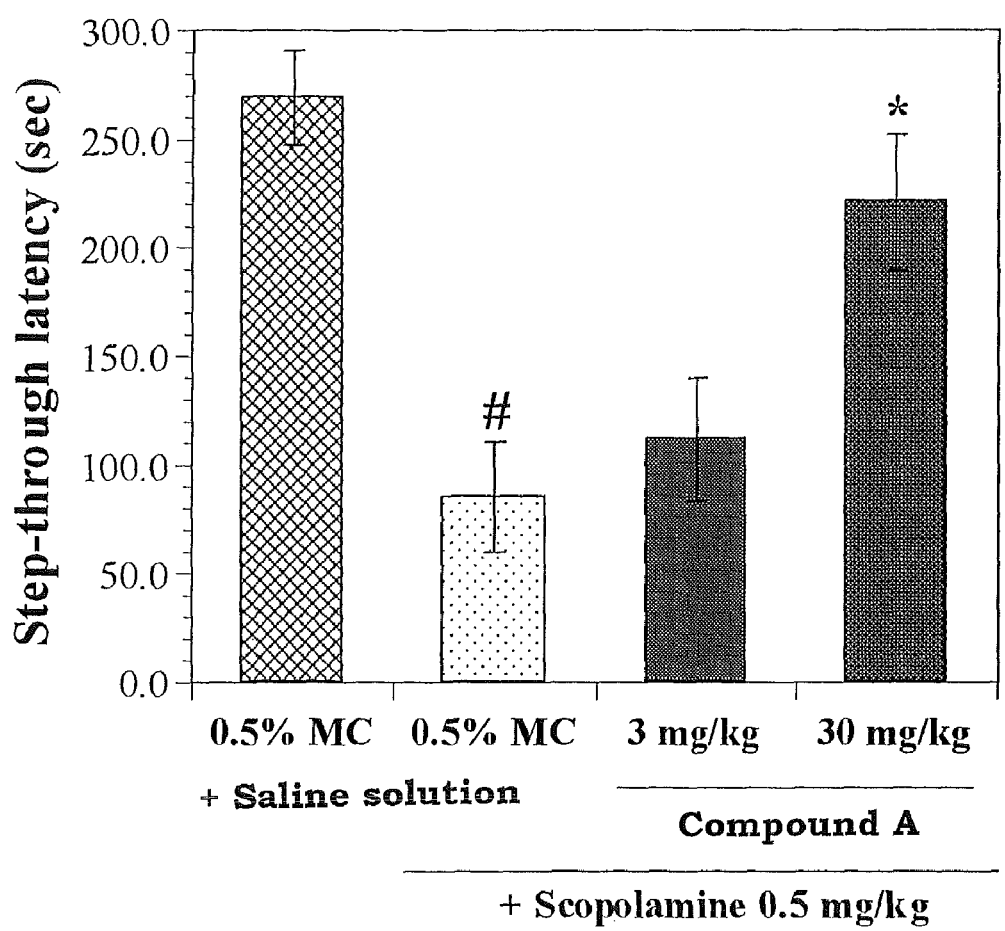
FIG. 2 shows the effects of the imide derivatives on rats in one step-through passive avoidance test where the acetylcholine receptor blocker scopolamine was used for inducing amnesia, and indicates the step-through latency during the test (*: P<0.05 vs the group treated with 0.5% MC+scopolamine (Steel's test), #: '<0.01 vs the group treated with 0.5% MC+saline solution (Mann-Whitney test)).

On Day 2 of the experiment, a test was carried out about 24 hours after the training. The procedures of the test were carried out in the same manner to the training step except that an electroconvulsive shock was not given. The step-through latency in the test was measured up to 300 seconds, and the step-through latency over 300 seconds was regarded as 300 seconds. FIG. 1 and FIG. 2 show the effects of Compound A on the scopolamine-induced cognitive/memory dysfunction models in the one step-through passive avoidance test when it was orally administered at a dosage of 3 mg/kg or 30 mg/kg. FIG. 1 shows the step-through latency during the training step, and FIG. 2 shows the step-through latency during the test. The number of the animals was 15 per group, and the data was expressed in mean±SEM.

Results

The agent for inducing amnesia, scopolamine did not affect on the step-through latency during the training. Compound A slightly shortened the step-through latency during the training step at a dose of 3 mg/kg. During the test, the animals treated with scopolamine showed a significantly shorter step-through latency as compared to the animals treated with saline solution (cognitive/memory dysfunction inducing effect). En the group treated with both of Compound A at a dose of 30 mg/kg and scopolamine, the step-through latency was significantly extended. That is, it was observed that Compound A exhibited an improving effect of scopolamine-induced cognitive/memory dysfunctions. Thus, it was found that the imide derivatives may exhibit an improving activity of scopolamine-induced cognitive/memory dysfunctions, and as a result, it may become apparent that the present invention may provide a therapeutic method for senile dementia and a therapeutic agent for said method.

INDUSTRIAL APPLICABILITY

According to the present invention, it was found that the imide derivatives may exhibit an improving activity of scopolamine-induced cognitive/memory dysfunctions, and as a result, it has become apparent that the present invention may provide a therapeutic method for senile dementia and a therapeutic agent for said method.

The invention claimed is:

1. A method for treatment of Alzheimer's-type dementia or dementia from Parkinson's disease, which comprises administering an effective amount of an imide compound of the formula [9]:

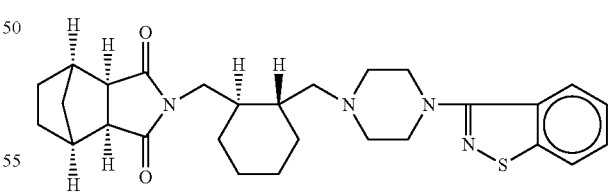

[9]

or an acid addition salt thereof to a mammal in need thereof.

2. The method according to claim 1, which is for the treatment of Alzheimer's-type dementia.

3. The method according to claim 1, which is for the treatment of dementia from Parkinson's disease.

4. The method according to claim 2, which is for the treatment of core symptoms of Alzheimer's-type dementia.

* * * * *